United States Patent [19]

Breuer et al.

[11] Patent Number: 5,539,135
[45] Date of Patent: Jul. 23, 1996

[54] PROCESS FOR PRODUCING HYDROPHOBICIZED DOUBLE-LAYER HYDROXIDE COMPOUNDS

[75] Inventors: Wolfgang Breuer, Duesseldorf; Claudia Mai, Meerbusch; Hans-Christian Raths, Monheim; Elvira Scholz, Duesseldorf, all of Germany

[73] Assignee: Henkel Kommanditgesellschaft auf Aktien, Duesseldorf, Germany

[21] Appl. No.: 129,058

[22] PCT Filed: Mar. 26, 1992

[86] PCT No.: PCT/EP92/00675

§ 371 Date: Oct. 4, 1993

§ 102(e) Date: Oct. 4, 1993

[87] PCT Pub. No.: WO92/17405

PCT Pub. Date: Oct. 15, 1992

[30] Foreign Application Priority Data

Apr. 4, 1991 [DE] Germany ............. 41 10 835.3

[51] Int. Cl.$^6$ ............................................ C11C 3/00
[52] U.S. Cl. ............. 554/167; 554/76; 554/149; 554/156; 554/170; 502/512; 502/506
[58] Field of Search ............... 554/149, 167, 554/156, 170, 76; 502/400, 401, 402, 414, 506, 512; 424/147

[56] References Cited

U.S. PATENT DOCUMENTS

| | | | |
|---|---|---|---|
| 4,351,814 | 9/1982 | Miyata et al. | 423/306 |
| 4,629,626 | 12/1986 | Miyata et al. | 424/147 |
| 4,962,237 | 10/1990 | Laycock | 568/618 |
| 5,292,910 | 3/1994 | Raths et al. | 554/149 |

FOREIGN PATENT DOCUMENTS

| | | |
|---|---|---|
| 0134936 | 3/1985 | European Pat. Off. |
| 0207811 | 1/1987 | European Pat. Off. |
| 0308646 | 3/1989 | European Pat. Off. |
| 0339426 | 11/1989 | European Pat. Off. |
| 1592126 | 10/1970 | Germany . |
| 3306822 | 8/1984 | Germany . |
| 3346943 | 7/1985 | Germany . |
| 3843713 | 11/1989 | Germany . |

OTHER PUBLICATIONS

J. Am. Oil. Chem. Soc. 63, 691 (1986).
Happi 52 (1986).
Chimia 24, 99 (1970).

*Primary Examiner*—José G. Dees
*Assistant Examiner*—Deborah D. Carr
*Attorney, Agent, or Firm*—Wayne C. Jaeschke; Norvell E. Wisdom, Jr.; Henry E. Millson, Jr.

[57] ABSTRACT

Hydrophobicized double-layer hydroxide compounds may be produced if double-layer hydroxide compounds of the general formula (I): $[M^{(II)}_{1-x}M^{(III)}_{x}(OH)_2] A_x \cdot n H_2O$, in which $M^{(II)}$ is a divalent metal cation, $M^{(III)}$ is a trivalent metal cation, A is an equivalent of a monobasic and/or multibasic inorganic acid, x is a number from 0.2 to 0.5 and n is a number from 0 to 10, are reacted at elevated temperature and under autogenous pressure with at least one carboxylic acid or its salt and the reaction product is then dried. The hydrophobicized double-layer hydroxide compounds obtained by this process are suitable as catalysts for the alkoxylation of compounds with active hydrogen atoms or of fatty acid esters.

28 Claims, No Drawings

PROCESS FOR PRODUCING HYDROPHOBICIZED DOUBLE-LAYER HYDROXIDE COMPOUNDS

This application is a 371 of PCT/EP92/00675 filed Mar. 3, 1992.

FIELD OF THE INVENTION

This invention relates to a process for the production of hydrophobicized double layer hydroxide compounds by reaction of double layer hydroxide compounds with carboxylic acids or salts thereof at elevated temperature and subsequent drying of the reaction products, and to the use of these compounds as catalysts in the alkoxylation of compounds containing active hydrogen atoms or of fatty acid esters.

STATEMENT OF RELATED ARTS

By virtue of their excellent detergent properties and their high solubility in cold water, adducts of ethylene and/or propylene oxide with primary alcohols, which are known as alcohol alkoxylates or alcohol polyglycol ethers, are acquiring increasing significance as nonionic surfactants for the production of laundry detergents, dishwashing detergents and cleaning products. However, in the course of the alkoxylation reaction, which is generally carried out in the presence of readily soluble alkali metal hydroxides or alcoholales, there is not selective addition of a discrete number of ethylene and/or propylene oxide units onto one molecule of the alcohol; instead the reaction follows statistical laws and leads to a mixture of homologous addition products of which the degrees of alkoxylation cover a broad spectrum.

It is known from *J. Am. Oil. Chem. Soc.* 63, 691 (1986) and *HAPPI* 52 (1986) that the distribution of the degrees of alkoxylation in the mixture of the alcohol alkoxylates, the so-called "homolog distribution", critically influences the properties of the addition products obtained. It has been found in this regard that products with a "narrow" homolog distribution, which are known as narrow-range alkoxylates, have advantages over comparable products with a "broad" homolog distribution, including for example:

lower pour points, higher smoke points, a smaller number of moles of alkylene oxide to achieve solubility in water, smaller contents of unreacted alcohol and hence reduced odor emission, and reduction of pluming during the spray drying of detergent slurries containing alcohol alkoxylate.

There has been no shortage of attempts in the past to produce adducts, of ethylene and/or propylene oxide with primary alcohols, which have a narrow homolog distribution and exhibit the described property profile, by variation of the alkoxylation catalyst.

Double layer hydroxide compounds, for example of the hydrotalcite type, have proved to be particularly effective heterogeneous catalysts, i.e. catalysts insoluble in the reaction mixture, for the production of narrow-range nonionic surfactants.

Thus, DE 38 43 713 A1 and U.S. Pat. No. 4,962,237 describe processes for the alkoxylalion of compounds containing active hydrogen atoms which are carried out in the presence of hydrotalcites. However, the hydrotalcites have to be converted beforehand into a calcined form suitable for catalytic purposes by heating for several hours to temperatures of 400° to 600° C. Although the narrow homolog distribution of the nonionic surfactants obtainable by this process may be regarded as satisfactory, production of the catalyst, particularly the calcination step, is both energy- and time-consuming and therefore disadvantageous. In addition, calcined compounds are susceptible to traces of water and to the carbon dioxide in the air (reverse reaction of the calcination), so that their range of application and stability in storage are limited by the loss of activity.

DESCRIPTION OF THE INVENTION
OBJECTION OF THE INVENTION

Accordingly, the problem addressed by the present invention was to provide a process for the production of activated double layer hydroxide compounds which would not have any of the disadvantages described above.

SUMMARY OF THE INVENTION

The present invention relates to a process for the production of hydrophobicized double layer hydroxide compounds which is characterized in that double layer hydroxide compounds corresponding to general formula (I):

$$[M^{(II)}_{1-x}M^{(III)}_x(OH)_2]A_x \cdot n\, H_2O \qquad (I),$$

in which $M^{(II)}$ is a divalent metal cation, $M^{(III)}$ is a trivalent metal cation, A is an equivalent of a monobasic and/or polybasic inorganic acid, x is a number of 0.2 to 0.5 and n is a number of 0 to 10, are reacted at elevated temperature and under autogenous pressure with a) at least one aliphatic monocarboxylic acid containing 2 to 24 carbon atoms or a salt thereof and/or b) at least one aliphatic dicarboxylic acid containing 4 to 48 carbon atoms or a salt thereof, and the reaction product is subsequently dried.

It has surprisingly been found that hydrophobicization of double layer hydroxides by the process according to the invention, i.e. reaction of the layer compounds with organic acids and subsequent drying, results in activation in the same way as could hitherto only be achieved by calcination. Whereas calcination requires temperatures of at least 400° C., the process according to the invention manages with temperatures of at most 250° C. and, accordingly, represents a distinct improvement in terms of the energy balance.

Double layer hydroxide compounds are understood to be polycations characterized by inner-crystalline charge equalization through mobile interlayer anions [Chimia 24, 99 (1970)].

DESCRIPTION OF PREFERRED EMBODIMENTS

Suitable divalent metal ions in formula (I) arc cations selected from the group consisting of magnesium, zinc, calcium, iron, cobalt, copper, cadmium, nickel and manganese. Double layer hydroxide compounds in which $M^{(II)}$ is magnesium arc preferably used.

Trivalent metal ions in formula (I) arc cations selected from the group consisting of aluminum, iron, chromium, manganese, bismuth and cerium. Double layer hydroxide compounds, in which $M^{(III)}$ is aluminum, are preferably used.

In formula (I), A stands for anions selected from the group consisting of carbonate, hydrogen carbonate, sulfate, nitrite, nitrate, phosphate, hydroxide and halides. Double layer hydroxide compounds in which A stands for carbonate are preferably used.

The preferred starting material for the production of the Hydrophobicized double layer hydroxide compounds by the process according to the invention is hydrotalcite—a substance which occurs as a mineral in nature and which may also be synthesized by appropriate methods, see DE 15 92 126 C, DE 33 46 943 A1, DE 33 06 822 A1 and EP 0 207 811 A1.

Ideally, hydrotalcite corresponds to formula (II):

$$[Mg_6Al_2(OH)_{16}]CO_3.4H_2O \qquad (II)$$

with a structure derived from that of brucite $[Mg(OH)_2]$. Brucite crystallizes in a layer structure with the metal ions in octahedral vacancies between two layers of close-packed hydroxyl ions, only every second layer of the octahedral vacancies being occupied. In hydrotalcite, some of the magnesium ions are replaced by aluminum ions so that the layer packet receives a positive charge. This is equalized by the anions present in the interlayers together with water of crystallization.

Other double layer hydroxide compounds which may be used as starting materials for the production of the Hydrophobicized species are, for example, magaldrate $[Mg_{10}Al_5(OH)_{30}](SO_4)_2OH.n\ H_2O$ pyroaurite $[Mg_6Fe_2(OH)_{16}]CO_3.4.5\ H_2O$ hydrocalumite $[Ca_2Al(OH)_6]NO_3.n\ H_2O$ Hydrophobicization is obtained by reaction of the double layer hydroxide compounds with aliphatic mono- or dicarboxylic acids or salts thereof.

Monocarboxylic acids. Monocarboxylic acids suitable for hydrophobicizing the double layer hydroxide compounds are aliphatic carboxylic acids containing 2 to 24 carbon atoms, of which typical examples are acetic acid, propionic acid, butyric acid, valeric acid, caproic acid, caprylic acid, capric acid, laurie acid, myristic acid, palmitic acid, palmitoleic acid, stearic acid, oleic acid, elaidic acid, petroselic acid, chaulmoogric acid, ricinoleic acid, linoleic acid, linolenic acid, arachic acid, gadoleic acid, behenic acid, erucic acid, arachidonic acid or clupanodonic acid. The monocarboxylic acids may also be used in the form of their salts, preferably their alkali metals salts and, more preferably, their sodium salts. Monocarboxylic acids containing 12 to 18 carbon atoms, particularly laurie acid, and sodium salts thereof are preferred.

As usual in oleochemistry, the monocarboxylic acids may also consist of the technical cuts which are obtained in the pressure hydrolysis of natural fats and oils, for example coconut oil, palm oil, palm kernel oil, cottonseed oil, peanut oil, soybean oil, rapeseed oil, sunflower oil, linseed oil, coriander oil, castor oil, beef tallow or fish oil. Technical $C_{12/18}$ and $C_{12/14}$ fatty acid mixtures based on coconut oil and sodium salts thereof are preferred.

Dicarboxylic acids. The hydrophobicization may also be carried out with dicarboxylic acids containing 4 to 48 carbon atoms, of which typical examples are succinic acid, maleic acid, fumaric acid, adipic acid, pimelic acid, suberic acid or sebacic acid. Other suitable dicarboxylic acids are so-called dimer fatty acids which are obtained, for example, by heating unsaturated fatty acids in the presence of montmorillonites and which may contain up to 48 carbon atoms. As already mentioned in reference to the monocarboxylic acids, the dicarboxylic acids may also be used in the form of their salts, preferably their alkali metal salts and, more preferably, their sodium salts.

The process according to the present invention seeks to provide hydrophobicized double layer hydroxides in which all monobasic or polybasic anions A in the compounds (I) are replaced by organic acid functions. For this reason, the double layer hydroxide compounds corresponding to formula (I) are reacted with the carboxylic acids or their salts in such quantities that hydrophobicized double layer hydroxide compounds containing 15 to 70% by weight and preferably 15 to 50% by weight of carboxylate, based on their total weight, are obtained.

To this end, it is advisable to react the double layer hydroxide compounds with the monocarboxylic acids or their salts in a molar ratio of 6:1 to 1:10 and, more particularly, 3:1 to 1:3 or with the dicarboxylic acids or their salts in a molar ratio of 3:1 to 1:5 and, more particularly, 1.5:1 to 1:3. The molar ratio has to be adjusted to the anions A of the particular double layer hydroxide compounds used which are available during the exchange.

To carry out the process according to the invention, it is sufficient initially to introduce the two components—double layer hydroxide compounds and carboxylic acids or carboxylic acid salts—into a pressure vessel, optionally in the form of a suspension in water, and to heat them over a period of 0.1 to 5 h and preferably over a period of 0.5 to 2 h under autogenous pressure to temperatures of 100° to 250° C. and preferably to temperatures of 150° to 220° C. It has proved to be of advantage to let off the gases (steam and carbon dioxide) released during the hydrophobicization process by partial venting of the autoclave.

The crude hydrophobicized product, which still contain residual moisture, is subsequently dried. This may be done, for example, in a drying chamber, optionally under reduced pressure, at temperatures of 100° to 220° C.

It can be shown by X-ray diffractograms that the hydrophobicized double layer hydroxide compounds have retained their layer structure with widening of the layer spacings.

The hydrophobicized double layer hydroxide compounds obtainable by the process according to the invention catalyze the alkoxylation of compounds containing active hydrogen atoms or of fatty acid esters.

Accordingly, the present invention relates to the use of these hydrophobicized double layer hydroxide compounds as catalysts in the alkoxylation of compounds containing active hydrogen atoms or of fatty acid esters.

The use of the hydrophobicized double layer hydroxide compounds produced in accordance with the invention enables compounds containing active hydrogen atoms and also fatty acid esters to be alkoxylated in high yields in short reaction times. The reaction products show an advantageous narrow homolog distribution, the distribution curve coming close to the ideal Poisson distribution. In addition, the reaction products are distinguished by small contents of unreacted starting materials and dioxane. The hydrophobicized double layer hydroxide compounds produced in accordance with the invention may readily be incorporated in the reaction mixture. Since they do not dissolve in the mixture, their separation, for example by filtration, is uncomplicated. However, they may even remain in the reaction mixture providing their presence does not adversely affect the subsequent use of the products.

Examples of compounds containing active hydrogen atoms, which may be alkoxylated in the presence of the hydrophobicized double layer hydroxide compounds obtainable by the process according to the invention, are fatty acids, hydroxyfatty acids, fatty acid amides, fatty alcohols, alkylphenols, polyglycols, fatty amines, fatty acid alkanolamides or vicinally hydroxy- or alkoxy-substituted alkanes.

Alkoxylation is an industrial process known per se which is carried out at temperatures of 120° to 220° C. and preferably at temperatures of 150° to 190° C. under pressures of 1 to 6 bars. The hydrophobicized double layer hydroxide compounds may be used in quantities of 0.1 to 3% by weight, based on the end product of the alkoxylation reaction.

In the interests of activity and a narrow homolog distribution, it has proved to be optimal to use a hydrotalcite (II) hydrophobicized with lauric acid as the hydrophobicized double layer hydroxide compound.

The following Examples are intended to illustrate the invention without limiting it in any way.

EXAMPLES

Example 1

Production of a hydrophobicized hydrotalcite catalyst.

A mixture of 50 g (0.08 mole) of hydrotalcite (commercial quality) and 32 g (0.16 mole) of lauric acid was introduced into an autoclave and suspended in 500 ml of water. The reaction mixture was heated to 200° C. over a period of 60 minutes under an autogenous pressure of 21 bar. The gases (carbon dioxide and steam) released from the reaction mixture were let off at intervals of about 15 minutes by venting to a pressure of 10 bar. On completion of the reaction, the reaction mixture was cooled, the hydrophobicized hydrotalcite was filtered off and was subsequently dried in a drying chamber first at 110° C. and then at 200° C. The yield of anhydrous hydrophobicized hydrotalcite was about 70 g.

Composition: Mg: 14.9% by weight
Al: 5.9% by weight
C: 33.1% by weight
Mg:Al ratio: 2.80:1.00
Mg:laurate ratio: 0.95:1.00

Example 2

Example 1 was repeated. However, the reaction of hydrotalcite and lauric acid was carried out over a period of 2 h.

Composition: Mg: 13.8% by weight
Al: 5.4% by weight
C: 30.8% by weight
Mg:Al ratio: 2.84:1.00
Mg:laurate ratio: 0.94:1.00

Comparison Example 1

20 g (0.033 mole) of a commercial hydrotalcite, which had been calcined for 2 h at 550° C., was suspended in 200 ml of water, and a solution of 25 g (0.125 mole) of lauric acid in 100 ml of isopropyl alcohol was added to the resulting suspension. The reaction mixture was heated for 3 h to 70° C., cooled and filtered off. After the filter cake had been washed with isopropyl alcohol, it was dried to constant weight at 100° C./100 hPa. The hydrophobicized hydrotalcite was obtained in the form of a colorless powder in a yield of about 42 g. The laurate content was about 44% by weight.

Example 3

In an autoclave, 2.5 g of the catalyst of Example 1 were suspended in 300 g (1.55 mole) of $C_{12/14}$ coconut oil fatty alcohol (Lorol®S, hydroxyl value 290, a product of Henkel KGaA). The reactor was purged with nitrogen and evacuated for 30 minutes at 100° C. The temperature was then increased to 150° C. and 204 g (4.6 moles) of ethylene oxide was introduced under pressure over a period of 20 minutes up to a pressure of 6 bars, the temperature rising to 180° C. Following an after-reaction lasting 30 minutes, the reaction mixture was cooled, vented and the catalyst filtered off.

Comparison Example 2

Example 3 was repeated with 300 g coconut oil fatty alcohol and 2.5 g of the catalyst of Comparison Example 1. In contrast to Example 3, a time of 90 minutes was required for the introduction under pressure of 204 g ethylene oxide.

The invention claimed is:

1. A process for the production of hydrophobicized double layer hydroxide compounds, wherein double layer hydroxide compounds corresponding to general formula (I):

$$(M^{(II)}_{1-x}M^{(III)}_x(OH)_2) A_{x^-}\cdot n\, H_2O \qquad (I),$$

in which $M^{(II)}$ is a divalent metal cation, $M^{(III)}$ is a trivalent metal cation, A is an equivalent of a monobasic or polybasic inorganic acid, x is a number of 0.2 to 0.5 and n is a number of 0 to 10, are reacted under autogenous pressure in a pressure vessel at a temperature in the range of from 100° to 250° C. with a) at least one aliphatic carboxylic acid containing 2 to 24 carbon atoms or b) at least one aliphatic dicarboxylic acid containing 4 to 48 carbon atoms, and the reaction product is subsequently dried.

2. A process as claimed in claim 1, in which $M^{(II)}$ is selected from the group consisting of magnesium, zinc, calcium, iron, cobalt, copper, cadmium, nickel and manganese.

3. A process as claimed in claim 2, in which $M^{(III)}$ is selected from the group consisting of aluminum, iron, chromium, manganese, bismuth and cerium.

4. A process as claimed in claim 3, in which A is selected from the group consisting of carbonate, hydrogen carbonate, sulfate, nitrite, nitrate, phosphate, hydroxide and halides.

5. A process as claimed in claim 4, wherein $C_{12-18}$ fatty acids are used as the carboxylic acids.

6. A process as claimed in claim 5, wherein the double layer hydroxide compounds corresponding to formula (I) are reacted with the carboxylic acids in such quantities that hydrophobicized double layer hydroxide compounds containing 15 to 70% by weight of carboxylate, based on their total weight, are obtained.

7. A process as claimed in claim 1, wherein the reaction of the double layer hydroxide compounds with the carboxylic acids is carried out at temperatures of 150° to 220° C.

8. A process as claimed in claim 7, wherein the drying step is carried out at temperatures of 100° to 220° C., optionally under reduced pressure.

9. A process as claimed in claim 1, in which $M^{(III)}$ is selected from the group consisting of aluminum, iron, chromium, manganese, bismuth and cerium.

10. A process as claimed in claim 1, in which A is selected from the group consisting of carbonate, hydrogen carbonate, sulfate, nitrite, nitrate, phosphate, hydroxide and halides.

11. A process as claimed in claim 1, wherein $C_{12-18}$ fatty acids are used as the carboxylic acids.

12. A process as claimed in claim 1, wherein the double layer hydroxide compounds corresponding to formula (I) are reacted with the carboxylic acids in such quantities that hydrophobicized double layer hydroxide compounds containing 15 to 70% by weight of carboxylate, based on their total weight, are obtained.

13. A process as claimed in claim 4, wherein the reaction of the double layer hydroxide compounds with the carboxylic acids is carried out at temperatures of 150° to 220° C.

14. A process as claimed in claim 1, wherein the drying step is carried out at temperatures of 100° to 220° C., optionally under reduced pressure.

15. In a process for alkoxylating compounds containing active hydrogen atoms or fatty acid esters, the improvement wherein a hydrophobicized double layer hydroxide compound obtained by the process of claim 1 is used as a catalyst therein.

16. A process as claimed in claim 15, wherein the compounds containing active hydrogen atoms are selected from the group consisting of fatty acids, hydroxyfatty acids, fatty acid amides, fatty alcohols, alkylphenols, polyglycols, fatty amines, fatty acid alkanolamides and vicinally hydroxy- or alkoxy-substituted alkanes.

17. A process as claimed in claim 16, wherein the hydrophobicized double layer hydroxide compounds are used in quantities of 0.1 to 3% by weight, based on the end product of the alkoxylation reaction.

18. A process as claimed in claim 17, wherein a hydrotalcite hydrophobicized with lauric acid is used as the hydrophobicized double layer hydroxide compound.

19. A process as claimed in claim 15, wherein the hydrophobicized double layer hydroxide compounds are used in quantities of 0.1 to 3% by weight, based on the end product of the alkoxylation reaction.

20. A process as claimed in claim 15, wherein a hydrotalcite hydrophobicized with lauric acid is used as the hydrophobicized double layer hydroxide compound.

21. A process for the production of hydrophobicized double layer hydroxide compounds, wherein double layer hydroxide compounds corresponding to formula (I):

$$(M^{(II)}_{1-x} M^{(III)}_x (OH)_2) A_x \cdot n\, H_2O \qquad (I),$$

in which $M^{(II)}$ is the magnesium cation, $M^{(III)}$ is the aluminum cation, A is an equivalent of a monobasic or polybasic inorganic acid, x is a number of 0.2 to 0.5 and n is a number of 0 to 10, are reacted under autogenous pressure in a pressure vessel at a temperature in the range of from 100° to 250° C. with at least one aliphatic carboxylic acid containing 12 to 18 carbon atoms, and the reaction product is subsequently dried.

22. The process of claim 21 wherein A in formula I is selected from the group consisting of carbonate, hydrogen carbonate, sulfate, nitrite, nitrate, phosphate, hydroxide and halides.

23. The process of claim 21 wherein the double layer hydroxide compounds corresponding to formula (I) are reacted with the carboxylic acids in such quantities that hydrophobicized double layer hydroxide compounds containing 15 to 70% by weight of carboxylate, based on their total weight are obtained.

24. The process of claim 21 wherein the reaction of the double layer hydroxide compounds with the carboxylic acids is carried out at temperatures of 150° to 220° C.

25. The process of claim 21 wherein the drying step is carried out at temperatures of 100° to 220° C., optionally under reduced pressure.

26. In a process for alkoxylating compounds containing active hydrogen atoms or fatty acid esters, the improvement wherein a hydrophobicized double layer hydroxide compound obtained by the process of claim 21 is used as a catalyst therein.

27. The process of claim 26 wherein the hydrophobicized double layer hydroxide compounds are used in quantities of 0.1 to 3% by weight, based on the end product of the alkoxylation reaction.

28. The process of claim 26 wherein a hydrotalcite hydrophobicized with lauric acid is used as the hydrophobicized double layer hydroxide compound.

* * * * *